United States Patent
December et al.

(10) Patent No.: US 7,485,336 B2
(45) Date of Patent: Feb. 3, 2009

(54) METHOD FOR PREDICTING AND OPTIMIZING CHIP PERFORMANCE IN CURED THERMOSET COATINGS

(75) Inventors: Timothy S. December, Rochester Hills, MI (US); Marc Bennett Fenwick, Commerce Township, MI (US); Yoshiko Kobayashi-San, Ann Arbor, MI (US); Scott Kubish, Michigan, MI (US); JoAnn Lanza, Farmington Hills, MI (US); Ippei Shinohara, Novi, MI (US)

(73) Assignees: BASF Corporation, Florham Park, NJ (US); Toyota Motor Engineering & Manufacturing North America, Inc., Ann Arbor, MI (US)

( * ) Notice: Subject to any disclaimer, the term of this patent is extended or adjusted under 35 U.S.C. 154(b) by 839 days.

(21) Appl. No.: 11/106,284

(22) Filed: Apr. 14, 2005

(65) Prior Publication Data

US 2006/0234404 A1 Oct. 19, 2006

(51) Int. Cl.
*B05D 5/00* (2006.01)
(52) U.S. Cl. .................. 427/8; 427/407.1; 427/409
(58) Field of Classification Search .................. 427/8, 427/407.1, 409
See application file for complete search history.

(56) References Cited

U.S. PATENT DOCUMENTS

| | | | | |
|---|---|---|---|---|
| 5,067,346 A | * | 11/1991 | Field | 73/81 |
| 5,149,382 A | * | 9/1992 | Gray | 148/257 |
| 2003/0012959 A1 | * | 1/2003 | Doty et al. | 428/423.1 |
| 2004/0236037 A1 | * | 11/2004 | December et al. | 525/525 |
| 2005/0123684 A1 | * | 6/2005 | Makowski et al. | 427/384 |

OTHER PUBLICATIONS

Tahmassebi et al., "Predicting the performances of basecoat/clearcoat automotive paint systems by the use of adhesion, scratch and mar resistance measurements," Polymer Degradation and Stability 83 (2004) 405-410.*

Ignatovich et al., "Material Surface Layer Damage Estimation For Cyclic Loading Conditions Using The Nanoindenting And Nanoscratching Techniques," Strength of Materials, vol. 38, No. 4, 2006, pp. 428-434.*

* cited by examiner

*Primary Examiner*—William Phillip Fletcher, III

(57) ABSTRACT

Disclosed is a method for evaluating chip performance of a cured coating system. In one embodiment, the method includes providing a coated substrate comprising a substrate and a cured film of a first coating composition thereon, measuring elastic work energy ($W_e/W_{tot}$) of the cured film, and calculating a % C.P. of the cured film via the formula: % C.P.=7.61636−0.225473 ($W_e/W_{tot}$) wherein a % C.P. of equal to or less than about 3.5% correlates to a total paint loss of equal to or less than 5% of a coating system comprising the first coating composition. The disclosed method predicts the gravelometer chip performance of a cured multilayer coating system comprising a first coating composition and a topcoat by measuring the measuring elastic work energy ($W_e/W_{tot}$) of the cured first coating system alone. In one embodiment, chip performance can be predicted without topcoat application and independent of topcoat composition.

19 Claims, No Drawings

METHOD FOR PREDICTING AND OPTIMIZING CHIP PERFORMANCE IN CURED THERMOSET COATINGS

FIELD OF THE INVENTION

The invention generally relates to thermoset coatings having improved chip performance, especially automotive coatings and more particularly to a method for predicting and evaluating chip performance in a cured thermoset film, especially in cured multilayer films.

BACKGROUND OF THE INVENTION

Curable thermoset coating compositions are widely used in the coatings art. They are often used as topcoats in the automotive and industrial coatings industry. Such topcoats may be basecoats, clearcoats, or mixtures thereof. Color-plus-clear composite coatings are particularly useful as topcoats where exceptional gloss, depth of color, distinctness of image, or special metallic effect is desired. The automotive industry has made extensive use of these coatings for automotive body panels.

Color-plus-clear composite coatings, however, require an extremely high degree of clarity in the clearcoat to achieve the desired visual effect. High-gloss coatings also require a low degree of visual aberrations at the surface of the coating in order to achieve the desired visual effect such as high distinctness of image (DOI). Finally, such composite coatings must also simultaneously provide a desirable balance of finished film properties such as chip performance, durability, hardness, flexibility, and resistance to environmental etch, scratching, marring, solvents, and/or acids.

Chip performance or gravel resistance is particularly important in automotive coatings, especially those intended for use on automotive components with leading edges, such as rocker panels and front bumpers. Weak or poor resistance to chipping can result in significant damage to the overall vehicle appearance and greatly reduced durability.

The prior art continues to seek an individual coating that provides improved chip resistance in a wide variety of coating systems employing various types of topcoats. More particularly, the prior art has yet to provide a way to improve chip resistance that is independent of the chemistry or molecular structure of the resin or binder component of a particular coating.

Of course, improvements in chip resistance must not be obtained at the expense of other important properties such as appearance and VOC.

In order to obtain the extremely smooth finishes that are generally required in the coatings industry, coating compositions must exhibit good flow before curing. Good flow is observed when the coating composition is fluid enough at some point after it is applied to the substrate and before it cures to a hard film to take on a smooth appearance. Some coating compositions exhibit good flow immediately upon application and others exhibit good flow only after the application of elevated temperatures.

One way to impart fluid characteristics and good flow to a coating composition is to incorporate volatile organic solvents into the composition. These solvents provide the desired fluidity and flow during the coating process, but evaporate upon exposure to elevated curing temperatures, leaving only the coating components behind.

However, the use of such solvents increases the volatile organic content (VOC) of the coating composition. Because of the adverse impact that volatile organic solvents may have on the environment, many government regulations impose limitations on the amount of volatile solvent that can be used. Increasing the percentage nonvolatile (% NV) of a coating composition or decreasing the VOC provides a competitive advantage with respect to environmental concerns, air permitting requirements, and cost.

There is thus a continuing desire to obtain thermoset coatings having an improved chip performance while still possessing the optimum balance of performance properties required by the automotive industry. This optimum balance of performance properties in the finished film must be obtained without sacrificing the Theological properties of the coating composition required for trouble-free application of the composition while still maintaining the optimum level of smoothness and appearance.

Unfortunately, the pursuit of such properties in a curable coating requires numerous experimental tests. The evaluation of chip resistance is typically conducted via a gravelometer test.

Gravelometer tests for automotive coatings generally require the placement of cured coated panels in a commercially available gravelometer. Gravel of a particular size and composition is then directed against the surface of a cold test panel. The size and frequency of resultant chipping is then evaluated, either via software or with the naked eye. Test panels for particular samples are normally done in triplicate.

However, the preparation of such gravelometer test panels continues to be a laborious and costly aspect of the development of automotive coating compositions having improved gravelometer performance.

Current automotive gravelometer testing practices typically require that all components of a cured multilayer coating system be applied and cured as required by the automotive manufacturer. These requirements are attributable to the prior art's failure to develop a method that correlates the individual gravelometer performance of a cured film of an individual component of a multilayer coating system to the gravelometer performance of the cured overall multilayer coating system.

For example, even though a set of test panels are intended solely to evaluate the gravelometer performance of particular primer compositions, each gravelometer test panel requires the application and curing of the specific primer composition followed by such topcoats as may be employed in a desired commercial multilayer coating system. The term 'multilayer coating system' as used herein generally refers to cured coating systems comprising a substrate, a primer, and a topcoat wherein the topcoat may comprise one or more sealers, monocoats, basecoats, color and/or effect coating compositions, clearcoat coating compositions, and combinations thereof. In one embodiment, an illustrative example of a commercially available automotive multilayer coating system will include an electrocoated steel substrate, a primer, and one or more applications of a wet-on-wet composite coating comprising a color and/or effect basecoat and a clearcoat.

As a result, the preparation of gravelometer test panels for the automotive coatings industry is normally a costly and lengthy process that requires the application, flashing, and curing of various other coating compositions in addition to the application and curing of the coating undergoing evaluation. Examples of illustrative 'other' coating compositions include any coatings that are utilized in multilayer automotive coating systems, i.e., sealers, basecoats, color and/or effect coating compositions, clearcoat coating compositions, and combinations thereof. The preparation of gravelometer tests panels thus continues to be a laborious and costly aspect of the development of automotive coating compositions having improved gravelometer performance.

It would therefore be advantageous to provide a method for evaluating the chip performance of a coated substrate that does not have the disadvantages of current gravelometer testing practices.

It would also be advantageous to develop a single measurement, nondestructive method for predicting the chip performance of a cured multilayer coating system by evaluating a particular property of one component of the cured multilayer coating system. It would be especially desirable if the evaluation of the one component was conducted without the use of current gravelometers or gravelometer testing practices but was predictive of the gravelometer performance of the overall cured multilayer coating system.

SUMMARY OF THE INVENTION

In one embodiment, a single measurement method is disclosed for predicting chip performance in a cured coating system comprising a first coating composition. In this embodiment, the disclosed method comprises providing a coated substrate comprising a substrate and a cured film of the first coating composition thereon, measuring elastic work energy ($W_e/W_{tot}$) of the cured film, and calculating a % C.P. of the cured film via the formula: % C.P.=7.61636−0.225473 ($W_e/W_{tot}$), wherein a % C.P. of equal to or less than about 3.50% correlates to a total paint loss of no more than 5% of a coating system comprising the first coating composition.

In another embodiment, the disclosed method predicts the gravelometer % paint loss of a cured multilayer coating system comprising a first coating composition without the use of a gravelometer. In this embodiment, the disclosed method consists essentially of providing a coated substrate consisting of an electrocoated substrate and a cured film of the first coating composition thereon, measuring elastic work energy ($W_e/W_{tot}$) of the cured film, and calculating a % C.P. of the cured film via the formula: % C.P.=7.61636−0.225473 ($W_e/W_{tot}$), wherein a % C.P. of equal to or less than about 3.10% correlates to a total paint loss of equal to or less than 2% of a multilayer coating system comprising a cured film of the first coating composition and a cured topcoat film.

DETAILED DESCRIPTION OF THE INVENTION

The following description of the preferred embodiment(s) is merely exemplary in nature and is in no way intended to limit the invention, its application, or uses. The singular forms "a", "an" and "the" include plural referents unless the context clearly dictates otherwise. "Optional" or "optionally" means that the subsequently described event or circumstance may or may not occur, and that the description includes instances where the event occurs and instances where it does not. The modifier "about" used in connection with a quantity is inclusive of the stated value and has the meaning dictated by the context (e.g., includes the degree of error associated with measurement of the particular quantity).

The term 'chip performance' as used herein refers to chip or gravel resistance. This performance property of a cured film or cured multilayer coating system has traditionally been evaluated according to a Gravelometer Chip Test, also referred to herein as 'gravelometer test'. The instantly disclosed method seeks to replace the % paint loss resulting from a gravelometer test with % Chip Performance or "C.P." as a measurement or indicator of chip performance. However, for such replacement to be meaningful, % C.P. must be correlated to % paint loss.

It will be appreciated that % paint loss refers to an evaluation of the total percentage of coated film removed as a result of a traditional gravelometer test. A traditional Gravelometer Chip Test or 'gravelometer test' is conducted as follows. A cured coated substrate is cooled to −20 degree C. for at least one hour prior to the test. The cold substrate is positioned in a test machine, referred to as a 'gravelometer', in an upright position, 90 degrees from the path of gravel. Three pints of gravel are then blown onto the cold substrate with an air pressure of 70 PSI. The gravel is preferably water-worn road gravel, not crushed limestone or rock, which will pass through a ⅝" space screen when grated, but will be retained on a ⅜" space screen. A suitable gravelometer is available from Q-Panel Lab Products. The test substrate is then analyzed using image software and a scanner. The substrate is scanned and the image software measures the percent paint film loss from the surface of the substrate.

In one embodiment, the percent paint film loss from a gravelometer test can be obtained by scanning the test substrate as a black and white drawing on a HP Scanjet™ 4c having a resolution of 75 dpi and a contrast of 125 (on a 0 to 250 scale), wherein HP DeskScan™ II V2.4 software is utilized for scanning. The scanned image of the substrate can then be analyzed using Visilog™ 5.1 software available from Noesis Vision, Inc. Analysis of the test substrate may be performed on a 12.5 by 6.8 cm area of the substrate. The percent film loss can be calculated using the "Area" routine in the software. The software calculates the percent paint film loss based on the number of dark pixels versus the total number of pixels (approx. 74,000).

Alternately, the substrate can be visually evaluated and measured on a scale. In one embodiment, visual standards may be employed to determine the percent paint or film loss.

However, as discussed above, current automotive gravelometer testing practices typically require that all components of a cured multilayer coating system be applied and cured as required by the automotive manufacturer. These requirements are attributable to the prior art's failure to develop a method that correlates the individual gravelometer performance of a cured film of an individual component of a multilayer coating system to the gravelometer performance of the cured overall multilayer coating system.

The method disclosed herein for predicting chip performance eliminates the need to prepare a test panel that comprises all of the film layer components of a cured multilayer coating system. As a result, the affect of various experimental parameters in a particular coating can be quickly and easily evaluated.

In one embodiment, a single measurement method is disclosed for predicting chip performance in a cured coating system comprising a first coating composition. In this embodiment, the disclosed method comprises providing a coated substrate comprising a substrate and a cured film of the first coating composition thereon, measuring elastic work energy ($W_e/W_{tot}$) of the coated substrate, and calculating a % C.P. of the coated substrate via the formula: % C.P.=7.61636−0.225473 ($W_e/W_{tot}$), wherein a % C.P. of equal to or less than about 2% correlates to a total paint loss of no more than 2% of a coating system comprising the first coating composition.

The disclosed method first requires the provision of a coated substrate or test panel. In one embodiment, the coated substrate will comprise a substrate and a cured film of a first coating composition.

Any curable coating compositions such as are known to those of skill in the art may be employed as the first coating composition of the disclosed method. It will be appreciated that the % C.P. will according to the particular composition of the selected first coating composition. Illustrative examples of coatings suitable for use as the first coating composition in the disclosed method include primers, basecoats, clearcoats, sealers, topcoats, monocoats, and combinations thereof. In one exemplary embodiment, the first coating composition will be a primer or sealer but especially a primer.

Coating compositions suitable for use as the first coating composition may be also characterized as one-component, two-component, multi-component, solvent borne, water borne, aqueous, solventless, powder coating, powder slurry coating, dispersion, emulsion, or combinations thereof. In one exemplary embodiment, the first coating composition will be a water borne coating or a one-component aqueous powder slurry coating.

In one embodiment, the first coating composition employed in the disclosed method will be a thermoset coating composition that is film forming. In one exemplary embodiment, the first coating composition forms a film when subject to energy, especially thermal energy, actinic radiation, or combinations thereof. The film-forming composition comprises a film-forming binder and a pigment mixture.

In one embodiment, the first coating composition will comprise a film-forming binder comprising one or more active hydrogen containing compounds, also referred to herein as crosslinkable resins, and one or more crosslinking agents.

"Active hydrogen group" as used herein refers to functional groups that donate a hydrogen group during the reaction with the functional groups of the one or more crosslinking agents. Examples of active hydrogen groups are carbamate groups, hydroxyl groups, amino groups, thiol groups, acid groups, hydrazine groups, activated methylene groups, and the like. Preferred active hydrogen groups are carbamate groups, hydroxyl groups, and mixtures thereof.

The one or more crosslinkable resins may be any crosslinkable resin suitable for use in a waterborne, solvent-based, powder coating composition, powder slurry composition, primer, topcoat, basecoat, or clearcoat. In one exemplary embodiment, the crosslinkable resin will be suitable for use in a primer composition, especially a waterborne or aqueous powder slurry composition.

As used herein, the term "crosslinkable resin" is intended to include not only those resins capable of being crosslinked upon application of heat but also those resins which are capable of being crosslinked without the application of heat. Examples of such crosslinkable resins include thermosetting acrylics, aminoplasts, carbamate functional resins, polyesters, epoxies, silicones and polyamides, modified acrylic polymers, polycarbonates, polyurethanes, polyimides, and polysiloxanes. These resins, when desired, may also contain functional groups characteristic of more than one class, as for example, polyester amides, urethane acrylates, carbamate acrylates, etc.

In one embodiment, the crosslinkable resin will be at least one of acrylic polymers, modified acrylics, or polyester polyurethane polymers. In another embodiment, the crosslinkable resin will be an acrylic or polyurethane polymer.

In one embodiment, the crosslinkable resin is an acrylic polymer. Suitable acrylic polymers may have a molecular weight of 500 to 1,000,000, and more preferably of 1500 to 50,000. As used herein, "molecular weight" refers to number average molecular weight, which may be determined by the GPC method using a polystyrene standard. Such polymers are well-known in the art, and can be prepared from monomers such as methyl acrylate, acrylic acid, methacrylic acid, methyl methacrylate, butyl methacrylate, cyclohexyl methacrylate, and the like. The active hydrogen functional group, e.g., hydroxyl, can be incorporated into the ester portion of the acrylic monomer. For example, hydroxy-functional acrylic monomers that can be used to form such polymers include hydroxyethyl acrylate, hydroxybutyl acrylate, hydroxybutyl methacrylate, hydroxypropyl acrylate, and the like. Amino-functional acrylic monomers would include t-butylaminoethyl methacrylate and t-butylamino-ethylacrylate. Other acrylic monomers having active hydrogen functional groups in the ester portion of the monomer are also within the skill of the art.

Modified acrylics can also be used as the crosslinkable resin. Such acrylics may be polyester-modified acrylics or polyurethane-modified acrylics, as is well known in the art. Polyester-modified acrylics modified with ε-caprolactone are described in U.S. Pat. No. 4,546,046 of Etzell et al, the disclosure of which is incorporated herein by reference. Polyurethane-modified acrylics are also well known in the art. They are described, for example, in U.S. Pat. No. 4,584,354, the disclosure of which is incorporated herein by reference.

Preferred carbamate functional acrylics useful as the crosslinkable resin can be prepared in a variety of ways. One way to prepare such polymers is to prepare an acrylic monomer having carbamate functionality in the ester portion of the monomer. Such monomers are well known in the art and are described, for example in U.S. Pat. Nos. 3,479,328, 3,674,838, 4,126,747, 4,279,833, and 4,340,497, 5,356,669, and WO 94/10211, the disclosures of which are incorporated herein by reference. One method of synthesis involves reaction of a hydroxy ester with urea to form the carbamyloxy carboxylate (i.e., carbamate-modified acrylic). Another method of synthesis reacts an unsaturated acid ester with a hydroxy carbamate ester to form the carbamyloxy carboxylate. Yet another technique involves formation of a hydroxyalkyl carbamate by reacting a primary or secondary amine or diamine with a cyclic carbonate such as ethylene carbonate. The hydroxyl group on the hydroxyalkyl carbamate is then esterified by reaction with acrylic or methacrylic acid to form the monomer. Other methods of preparing carbamate-modified acrylic monomers are described in the art, and can be utilized as well. The acrylic monomer can then be polymerized along with other ethylenically unsaturated monomers, if desired, by techniques well known in the art.

An alternative route for preparing one or more polymers or oligomers useful as the crosslinkable resin is to react an already-formed polymer such as an acrylic polymer with another component to form a carbamate-functional group appended to the polymer backbone, as described in U.S. Pat. No. 4,758,632, the disclosure of which is incorporated herein by reference. Another technique for preparing polymers useful as the crosslinkable resin involves thermally decomposing urea (to give off ammonia and HNCO) in the presence of a hydroxy-functional acrylic polymer to form a carbamate-functional acrylic polymer. Another technique involves reacting the hydroxyl group of a hydroxyalkyl carbamate with the isocyanate group of an isocyanate-functional acrylic or vinyl monomer to form a carbamate-functional acrylic. Isocyanate-functional acrylics are known in the art and are described, for example in U.S. Pat. No. 4,301,257, the disclosure of which is incorporated herein by reference. Isocyanate vinyl monomers are well known in the art and include unsaturated m-tetramethyl xylene isocyanate (sold by American Cyanamid as TMI®). Yet another technique is to react the cyclic carbonate group on a cyclic carbonate-functional acrylic with ammonia in order to form the most preferred carbamate-functional acrylic. Cyclic carbonate-functional acrylic polymers are known in the art and are described, for example, in U.S. Pat. No. 2,979,514, the disclosure of which is incorporated herein by reference. Another technique is to transcarbamylate a hydroxy-functional acrylic polymer with an alkyl carbamate. A more difficult, but feasible way of preparing the polymer would be to trans-esterify an acrylate polymer with a hydroxyalkyl carbamate.

In one embodiment, polymers useful as the crosslinkable resin will generally have a number average molecular weight of 2000-20,000, and preferably from 3000-6000. The carbamate content of the polymer, on a molecular weight per equivalent of carbamate functionality, will generally be between 200 and 1500, and preferably between 300 and 500.

Polyesters having active hydrogen groups such as hydroxyl groups can also be used as the crosslinkable resin in the disclosed coating composition. Such polyesters are well known in the art, and may be prepared by the polyesterification of organic polycarboxylic acids (e.g., phthalic acid, hexahydrophthalic acid, adipic acid, maleic acid) or their anhydrides with organic polyols containing primary or secondary hydroxyl groups (e.g., ethylene glycol, butylene glycol, neopentyl glycol).

Carbamate functional polyesters are also suitable for use as the crosslinkable resin in the first coating compositions. Suitable polyesters can be prepared by the esterification of a polycarboxylic acid or an anhydride thereof with a polyol and/or an epoxide. The polycarboxylic acids used to prepare the polyester consist primarily of monomeric polycarboxylic acids or anhydrides thereof having 2 to 18 carbon atoms per molecule. Among the acids that are useful are phthalic acid, hexahydrophthalic acid, adipic acid, sebacic acid, maleic acid, and other dicarboxylic acids of various types. Minor amounts of monobasic acids can be included in the reaction mixture, for example, benzoic acid, stearic acid, acetic acid, and oleic acid. Also, higher carboxylic acids can be used, for example, trimellitic acid and tricarballylic acid. Anhydrides of the acids referred to above, where they exist, can be used in place of the acid. Also, lower alkyl esters of the acids can be used, for example, dimethyl glutarate and dimethyl terephthalate.

Polyols that can be used to prepare suitable polyesters include diols such as alkylene glycols. Specific examples include ethylene glycol, 1,6-hexanediol, neopentyl glycol, and 2,2-dimethyl-3-hydroxypropyl-2,2-dimethyl-3-hydroxypropionate. Other suitable glycols include hydrogenated bisphenol A, cyclohexanediol, cyclohexanedimethanol, caprolactone-based diols such as the reaction product of e-caprolactone and ethylene glycol, hydroxy-alkylated bisphenols, polyether glycols such as poly(oxytetramethylene)glycol, and the like.

Although the polyol component can comprise all diols, polyols of higher functionality can also be used. It is preferred that the polyol be a mixture of at least one diol and at least one triol, or one polyol of higher functionality. Examples of polyols of higher functionality would include trimethylol ethane, trimethylol propane, pentaerythritol, and the like. Triols are preferred. The mole ratio of polyols of higher functionality to diol is generally less than 3.3/1, preferably up to 1.4/1.

Carbamate groups can be incorporated into the polyester by first forming a hydroxyalkyl carbamate that can be reacted with the polyacids and polyols used in forming the polyester. A polyester oligomer can be prepared by reacting a polycarboxylic acid such as those mentioned above with a hydroxyalkyl carbamate. An example of a hydroxyalkyl carbamate is the reaction product of ammonia and propylene carbonate. The hydroxyalkyl carbamate is condensed with acid functionality on the polyester or polycarboxylic acid, yielding terminal carbamate functionality. Terminal carbamate functional groups can also be incorporated into the polyester by reacting isocyanic acid with a hydroxy functional polyester. Also, carbamate functionality can be incorporated into the polyester by reacting a hydroxy functional polyester with urea.

Carbamate groups can also be incorporated into the polyester by a transcarbamalation reaction. In this reaction, a low molecular weight carbamate functional material derived from a low molecular weight alcohol or glycol ether such as methyl carbamate is reacted with the hydroxyl groups of a hydroxyl functional polyester, yielding a carbamate functional polyester and the original alcohol or glycol ether. The low molecular weight carbamate functional material derived from an alcohol or glycol ether is first prepared by reacting the alcohol or glycol ether with urea in the presence of a catalyst. Suitable alcohols include lower molecular weight aliphatic, cycloaliphatic, and aromatic alcohols such as methanol, ethanol, propanol, butanol, cyclohexanol, 2-ethylhexanol, and 3-methylbutanol. Suitable glycol ethers include ethylene glycol methyl ether and propylene glycol methyl ether. Propylene glycol methyl ether is preferred.

Besides carbamate functionality, polyester polymers and oligomers suitable for use as the crosslinkable resin may contain other functional groups such as hydroxyl, carboxylic acid and/or anhydride groups. The equivalent weight of such polyesters containing terminal carbamate groups may be from about 140 to 2500, based on equivalents of carbamate groups. The equivalent weight is a calculated value based on the relative amounts of the various ingredients used in making the polyester, and is based on the solids of the material.

Polyurethanes having active hydrogen functional groups such as described above which are suitable for use as the crosslinkable resin are also well known in the art. They are prepared by a chain extension reaction of a polyisocyanate (e.g., hexamethylene diisocyanate, isophorone diisocyanate, MDI, etc.) and a polyol (e.g., 1,6-hexanediol, 1,4-butanediol, neopentyl glycol, trimethylol propane). They can be provided with active hydrogen functional groups by capping the polyurethane chain with an excess of diol, polyamine, amino alcohol, or the like.

Carbamate functional polyurethanes may be prepared by reacting the active hydrogen groups with a low molecular weight carbamate functional material derived from a low molecular weight alcohol or glycol ether such as methyl.

Other carbamate functional compounds preferred for use as a crosslinkable resin are carbamate-functional compounds which are the reaction product of a mixture comprising a polyisocyanate or a chain extended polymer, and a compound comprising a group that is reactive with isocyanate or a functional group on the chain extended polymer as well as a carbamate group or group that can be converted to carbamate. Such compounds are described in U.S. Pat. Nos. 5,373,069 and 5,512,639 hereby incorporated by reference.

In one exemplary embodiment, the crosslinkable resin may be at least one of carbamate functional acylics, carbamate functional modified acrylics, hydroxyl functional acrylics, hydroxyl functional modified acrylics, polyurethanes, polyesters and mixtures thereof.

In one exemplary embodiment, the first coating composition will crosslink either by itself i.e., self crosslinking, or with a crosslinking agent. In one embodiment, the first coating composition will thus comprise one or more crosslinking agents having one or more crosslinkable functional groups. Such groups include, for example, hydroxy, isocyanate, amine, epoxy, acrylate, vinyl, silane, and acetoacetate groups. Such groups may be blocked or unblocked. In one embodiment, such functional groups may be masked or blocked in such a way as to become unblocked and available for crosslinking under a desired curing condition or event, generally elevated temperatures.

Useful crosslinkable functional groups include hydroxy, epoxy, acid, anhydride, silane, and acetoacetate groups and/or active methylol or methylalkoxy groups. In one embodiment, suitable crosslinking agents will have at least one crosslinkable functional groups selected from hydroxy functional groups, amino functional groups, isocyanate groups, and active methylol or methylalkoxy groups.

Illustrative crosslinkers include, without limitation, melamine formaldehyde crosslinkers, including monomeric or polymeric melamine resin and partially or fully alkylated melamine resin, urea resins, and methylol ureas such as urea formaldehyde resin, alkoxy ureas such as butylated urea formaldehyde resin, and polyisocyanates and blocked polyisocyanates. The curing agent may be a combination of the foregoing. In one exemplary embodiment, the crosslinking agent of the film-forming binder will be at least one of a polyisocyanates or an aminoplast resin.

In one embodiment, the crosslinking agent is at least about 5%, more preferably at least about 10% by weight of the nonvolatile binder or vehicle, with the remainder of the nonvolatile binder being comprised of the crosslinkable resin. "Nonvolatile vehicle" refers to the solid portion of the film-forming or crosslinking components of the binder. It is also preferred for the crosslinking agent to be up to about 40%, more preferably up to about 30% by weight of the nonvolatile vehicle. In one embodiment, the crosslinking agent is preferably from about 5% to about 40% by weight of the nonvolatile vehicle.

In one exemplary embodiment, the first coating composition will further comprise a pigment mixture. In one embodiment, the pigment mixture consists of (i) titanium dioxide and (ii) non-titanium dioxide pigments.

In one exemplary embodiment, the pigment mixture will consist of pigment particles having a particle shape that is as close to spherical as possible. It will be appreciated that pigment particles having platelet shape or elliptical shapes are favored over block shaped pigment particles. In one exemplary embodiment, the pigment mixture will consist of pigments having spherical particles.

In one exemplary embodiment, the pigment mixture will be substantially free of any coloring pigment, effect pigment, filler pigment, and extender pigment other than pigments (i) and (ii). In another exemplary embodiment, the film-forming coating composition will be substantially free of any coloring pigment, effect pigment, filler pigment, and extender pigment other than pigments (i) and (ii) present in the pigment mixture.

Pigment (i) consists of titanium dioxide ($TiO_2$). Suitable titanium dioxides include those commercially available for use in film-forming coating applications. Suitable titanium dioxides may be characterized by excellent color, opacity, dispersibility, heat stability, light fastness, high refractive index, and resistance to chemicals, acids, and alkali materials. In one exemplary embodiment, the titanium dioxide pigment (i) will be rutile titanium dioxide. In one especially exemplary embodiment, the titanium dioxide pigment (i) will be rutile titanium dioxide having spherical particles and a refractive index of at least about 2.5, more especially of at least about 2.75.

In one embodiment, the non-titanium dioxide pigments are selected from the group consisting of carbon black, talc, barium sulfate, magnesium silicate, and combinations comprising two or more of the foregoing. In one exemplary embodiment, the non-titanium dioxide pigment will be either barium sulfate or talc. In one especially exemplary embodiment, the non-titanium dioxide pigment (ii) will be barium sulfate.

In one exemplary embodiment, the pigment mixture consists of (i) at least about 80% of titanium dioxide by weight, based on the total weight of the pigment mixture, and (ii) no more than about 20% by weight of non-titanium dioxide pigments based on the total weight of the pigment mixture. In another embodiment, the pigment (i) will be present in an amount from about 80% to about 100% by weight, while pigment (ii) may be present in an amount from about 20% to about 0% by weight, all based on the total weight of the pigment mixture. In one especially exemplary embodiment, the pigment (ii) will be minimized to the extent possible. In another especially exemplary embodiment, the pigment (i) will be present in an amount from about 85% to about 95% by weight, based on the total weight of the pigment mixture.

The pigment mixture is present in the film-forming first coating composition in an amount such that the composition has a pigment to binder (P/B) ratio of at least about 0.8. The P/B ratio is based upon the amount of solid pigment to the amount of film-forming binder. In another embodiment, the pigment mixture is present in an amount sufficient to provide a P/B ratio less than the Critical Pigment Volume Concentration (CPVC). The volume concentration or volume fraction of dispersed solid pigment phase in the polymeric binder of the coating is normally defined as the pigment volume concentration (PCV). CPVC may be defined as that concentration of pigments where there is just sufficient polymer matrix to wet and fill the voids between the individual particles.

In one exemplary embodiment, the pigment mixture will be present in an amount sufficient to provide a P/B ratio of less than about 0.95. In another exemplary embodiment, the pigment mixture is present in an amount sufficient to provide a P/B ratio of from about 0.85 to about 0.95.

While not wishing to be bound to a particular theory, it is believed that P/B ratios of the disclosed pigment mixture of less than about 0.8 result in cured films and multilayer coating systems using such cured films that have a less than optimized chip performance. P/B ratios greater than the CPVC are also believed to produce cured films having less than optimum chip performance.

Other materials well-known to the coatings artisan, for example, surfactants, stabilizers, wetting agents, dispersing agents, adhesion promoters, UV absorbers, light stabilizers such as HALS, antioxidants, solvents, catalysts, and/or rheology control agents, may be incorporated into the first coating composition so long as the foregoing considerations as to the pigment mixture are observed. The amount of these materials used must be controlled to achieve the desired performance properties and/or to avoid adversely affecting the coating characteristics.

A solvent or solvents may be utilized in the first coating composition. In general, the solvent can be any organic solvent and/or water. In one preferred embodiment, the solvent includes a polar organic solvent. In another embodiment, the solvent includes one or more organic solvents selected from polar aliphatic solvents or polar aromatic solvents. In one embodiment, the solvent includes a ketone, ester, acetate, aprotic amide, aprotic sulfoxide, aprotic amine, or a combination of any of these. Examples of useful solvents include, without limitation, methyl ethyl ketone, methyl isobutyl ketone, m-amyl acetate, ethylene glycol butyl ether-acetate, propylene glycol monomethyl ether acetate, xylene, N-methylpyrrolidone, blends of aromatic hydrocarbons, and mixtures of these. In one especially exemplary embodiment, the solvent is water or a mixture of water with small amounts of co-solvents.

In one exemplary embodiment, the first coating composition will have a low VOC. A 'low VOC' as used herein refers to a film-forming composition having an adjusted VOC of no more than 100 g/L of volatile organic solvent. Adjusted VOC as used herein refers to the concentrationn of volatile organic solvent per L of coating composition not including water.

Notwithstanding the low VOC requirements, in one exemplary embodiment, the disclosed first coating composition will have a viscosity of no more than about 200 cps at 384 $sec^{-1}$. In one especially exemplary embodiment, the film-forming first coating composition will have a viscosity of from about 110 cps to about 160 cps at 384 $sec^{-1}$.

Regardless of the particular composition employed as the first coating composition, it is applied to a substrate for the practice of the disclosed method.

Suitable substrates for use in the disclosed method include all automotive substrates, including but not limited to metal substrates, plastic substrates, and combinations thereof. Automotive substrates are especially suitable in as much as automobiles have predetermined areas, such as rocker panels and leading edges, which are more susceptible to becoming chipped and would benefit from the application of film-forming coating compositions or multilayer coating systems having improved chip resistance. The disclosed coating compositions may be applied to aluminum and galvanized steel. The primer, sealer, or anti-chip compositions disclosed herein may also be applied to automotive plastic substrates such as bumpers, mirror housings, or internal dashboards. Metal substrates such as steel or galvanized steel are used in one exemplary embodiment as the substrate in the disclosed method.

The test substrate to which the first coating composition is applied may be bare, pretreated, and/or coated with an applied electrodeposition coating as are known in the art. Such electrodeposition coatings may be cationic or anionic, with cationic electrodeposition coatings being used in one exemplary example.

The first coating composition can be applied to the substrate by any of a number of techniques well known in the art. These include, for example, spray coating, dip coating, roll coating, curtain coating, and the like. For automotive body panels, spray coating is preferred. When the coatings will be relatively thick, they are usually applied in two or more coats separated by a time sufficient to allow some of the water and/or solvent evaporate from the applied coating layer ("flash"). The coats as applied are usually from 1 to 3 mils of the coating composition, and a sufficient number of coats are applied to yield the desired final coating thickness.

In one embodiment, the first coating compositions will be employed as a primer and will be applied to the test substrate so as to have a dry film build of from about 0.5 to about 5 mils. In one embodiment, the dry film build is from 0.8 to 4 mils, while in one exemplary embodiment the dry film build of the disclosed first coating composition is from about 1 to about 3 mils.

The first coating composition that is applied to the substrate is cured to provide the required coated substrate that comprises a cured film of the first coating composition. Curing may be achieved per any acceptable curing means as known to those of skill in the art and as are applicable to the selected first coating composition. The term 'film' as used herein refers to a layer of a cured coating composition. In one exemplary embodiment, a film is a crosslinked layer that is reasonably resistant to attack by a solvent such as methyl ethyl ketone (MEK).

In one embodiment, curing refers to the application of a stimulus such as thermal energy, electromagnetic energy or a combination thereof. Electromagnetic energy as used herein refers to actinic radiation and corpuscular radiation such as electron beam. In one exemplary embodiment, the first coating composition will be curable upon the application of thermal energy.

Substrates coated with an electrodeposition coating may be cured before or after the application of the first coating composition. For example, the electrodeposition coating and the applied first coating composition may be cured concurrently with the application of thermal energy for a time sufficient to affect crosslinking in both coatings. In one exemplary embodiment, the first coating composition comprising a binder and a pigment mixture as described above will be applied to a test substrate having a cured electrodeposition coating thereon, wherein the first coating composition is applied to the film of the cured electrodeposition coating.

In one exemplary embodiment, the test panel is flashed for three minutes in ambient conditions and then flashed for five minutes at 122 degree F. (50 C) followed by baking for thirty minutes in an oven at 302 degree F. (150 C) to provide the coated substrate.

In one embodiment, the coated substrate may comprise other films of cured coating compositions in addition to the film of the cured first coating composition. For example, the coated substrate may comprise one or more additional cured layers of other multilayer coating system components such as primers, topcoats, basecoats, clearcoats, sealers, and combinations thereof.

However, in one embodiment, the coated substrate will not contain any further cured coating compositions or films other than the film of the cured first coating composition. In another embodiment, the coated substrate will consist of a substrate and a cured film of the first coating composition. In one exemplary embodiment, the coated substrate will consist of an electrocoated substrate and a cured film of the first coating composition.

The disclosed method requires that elastic work energy ($W_e/W_{tot}$) of the coated substrate measured. In one exemplary embodiment of the disclosed method, the elastic work energy ($W_e/W_{tot}$) of the cured film of the first coating composition will be measured.

In one embodiment, elastic work energy refers to the ratio of the elastic work divided by the total work done as a result of the indentation of a hard body. In one embodiment, the hard body will be a diamond Vickers pyramid.

In one embodiment, the elastic work energy may be calculated via the measurement of microhardness. Microhardness may be calculated using a indentor or nanoindentor.

However, in one exemplary embodiment, elastic work energy ($W_e/W_{tot}$) will be measured using a Fischer microhardness tool or any commercially available equivalent. The term "Fischer microhardness tool" as used herein refers to the commercially available products of H. Fischer GmbH—Sindelfingen. An illustrative example of a suitable Fischer microhardness tool is the Fischerscope™ H100 SMC available from H. Fischer GmbH. I Relevant measurements can be obtained with a suitable Fischer microhardness tool as follows: a cured coated test panel is placed face down on a stage and evaluated using a Vicker diamond pyramid applied at 25.000 mN/20s. Suitable test panels will have a dry film build from about 0.8 to 2.0 mils and may be prepared by the application and curing of the above discussed first coating composition to a suitable substrate as discussed above at cure schedules of from 140 degrees C to 160 degrees C for 15 to 30 minutes. In one exemplary embodiment, no other coatings are applied during the preparation of the test panels. Measurements are obtained using WIN-HCU™ software.

In one exemplary embodiment of the disclosed method, a Fischer microhardness tool will be utilized to provide a value for elastic work energy ($W_e/W_{tot}$).

In another embodiment, other parameters besides elastic work energy will be obtained. Illustrative examples of other values that may be obtained by a Fischer microhardness tool or a commercially available equivalent include one or more of universal hardness, maximum indentation, Creep at maximum force, Creep at minimum force, Young's Modulus, or a combination of two or more of the foregoing, in addition to elastic work energy ($W_e/W_{tot}$). In one exemplary embodiment, the step of measuring the elastic work energy will comprise obtaining values for universal hardness, maximum indentation, Creep at maximum force, Creep at minimum force, and Young's Modulus, in addition to measuring elastic work energy ($W_e/W_{tot}$).

In one embodiment, the measured elastic work energy ($W_e/W_{tot}$) will be at least 20%. In general, a higher value for elastic work energy ($W_e/W_{tot}$) is desired. In one exemplary embodiment, the measured elastic work energy ($W_e/W_{tot}$) will be from about 20% to about 35%.

The value of % C.P. is calculated per % C.P.=7.61636−0.225473 ($W_e/W_{tot}$). In one embodiment, the % C.P. will be no more than 3.50. In another embodiment, the % C.P will be no more than 3.10. In one exemplary embodiment, the % C.P. will be from about 0 to about 3.10. In another exemplary embodiment, the % C.P. will be from about 0 to about 2.50. In one especially exemplary embodiment, the % C.P. of a coated substrate will be from about 0 to about 2.00 or less. It will be appreciated that any negative numbers obtained for % C.P. will be treated as zero.

The % C.P. of a cured film has been found to correlate to the % paint loss of a cured film evaluated by a traditional gravelometer test as described herein. As indicated below in the Examples, it has been found that a % C.P. of no more than 3.5% correlates to a total paint loss of no more than 5% as evaluated by a gravelometer test as described herein. In one embodiment, a % C.P. of no more than 2.50% correlates to a total paint loss of no more than 1.0% as evaluated by a gravelometer test as described herein.

In one embodiment, the % C.P. of the cured film of the first coating composition will correlate to a gravelometer % paint loss for a multilayer coating system comprising a cured film of the first coating composition. In one exemplary embodiment, a % C.P. of no more than 3.5 for a cured film of the first coating composition will correlate to a gravelometer % paint loss of no more than 5% for a multilayer coating system comprising a cured film of the first coating composition. In another exemplary embodiment, a % C.P. of no more than 2.50 for a cured film of the first coating composition will correlate to a gravelometer % paint loss of no more than 1.0% for a multilayer coating system comprising a cured film of the first coating composition.

In one embodiment, a cured film having a % C.P of no more than 3.10 has a desirable chip performance while those having a % C.P. greater than about 3.5 may be characterized as having poor or undesirable chip performance Multilayer coating systems utilizing the disclosed first coating compositions can be prepared to provide improved chip performance. As indicated above, it is expected that the gravelometer % paint loss of these cured multilayer coating systems will correlate to the % C.P. of the cured film of the first coating composition. In one exemplary embodiment, the disclosed film-forming first compositions will be used as primer, sealer, or anti-chip coating compositions, especially low VOC water borne or aqueous powder slurry primer compositions, in multilayer coating systems. In one exemplary embodiment, the disclosed first coating compositions will be characterized by the presence of the binder and pigment mixture discussed above in the disclosed P/B ratio.

In one embodiment, a multilayer coating system evaluated by the disclosed method will comprise a topcoat layer applied to the applied layer of the first coating composition. The topcoat layer serves both aesthetic and functional purposes such as increasing gloss and resistance to acid-etch, respectively. In one embodiment, the topcoat layer is applied to the first coating composition layer and cured, either concurrently or simultaneously.

In one embodiment, the topcoat may be a composite coating comprising a basecoat composition and clearcoat composition. The basecoat layer may contain one or more colorant and/or effect pigments as discussed above. The clearcoat layer is a transparent coating that provides an attractive smooth and glossy finish to the substrate and is applied to the basecoat layer.

In one embodiment the basecoat layer and the clearcoat layer will be applied wet-on-wet. The layers are applied in coats separated by a flash, as described below, with a flash also between the last coat of the color composition and the first clearcoat layer. The two coating layers are then cured simultaneously. In one embodiment, the film build of the cured basecoat layer is from about 0.6 to about 1.6 mils, while in another embodiment it is from about 0.8 to about 1.4 mils thick. The dry film build of the cured clear coat layer in one embodiment is from about 1 to about 3 mils, while in a more exemplary embodiment it is from about 1.4 to about 2.4 mils.

The applied first coating composition employed as a primer and a topcoat can be applied wet-on-wet. For example, the primer composition can be applied and flashed, followed by application and flashing of the topcoat, followed by curing of the primer and topcoat at the same time. Again, the topcoat can include the basecoat layer and the clearcoat layer applied wet-on-wet.

It is also to be understood that different types of topcoats are compatible with the variously disclosed first coating compositions. These different types include, but are not limited to, one-component solvent borne clearcoats, one-component waterborne clearcoats, two-component solvent borne clearcoats, and two-component waterborne clearcoats. In one exemplary embodiment, the topcoat will be a composite basecoat clearcoat coating.

In one exemplary embodiment, the topcoat is a crosslinking composition. Polymers known in the art to be useful in basecoat and clearcoat compositions include, without limitation, acrylics, vinyls, polyurethanes, polycarbonates, polyesters, alkyds, and polysiloxanes. Acrylics and polyurethanes are preferred. Thermoset basecoat and clearcoat compositions are also preferred, and, to that end, preferred polymers comprise one or more kind of crosslinkable functional groups, such as carbamate, hydroxy, isocyanate, amine, epoxy, acrylate, vinyl, silane, acetoacetate, and so on. The polymer may be self-crosslinking, or, preferably, the composition may include a crosslinking agent such as a polyisocyanate or an aminoplast resin of the kind described above.

Pigmented topcoats or basecoats used in the disclosed method may include one or more pigments well-known in the art, such as inorganic pigments like titanium dioxide, carbon black, and iron oxide pigments, or organic pigments like azo reds, quinacridones, perylenes, copper phthalocyanines, carbazole violet, monoarylide and diarylide yellows, naphthol orange, and the like, as well as effect pigments such as mica and the like.

Other materials well-known to the coatings artisan, for example, surfactants, fillers, stabilizers, wetting agents, dispersing agents, adhesion promoters, UV absorbers, light stabilizers such as HALS, antioxidants, solvents, catalysts, and/or rheology control agents, may also be incorporated into the topcoats or composite coatings used in the disclosed method. The amount of these materials used must be controlled to achieve the desired performance properties and/or to avoid adversely affecting the coating characteristics.

Each layer of the multilayer coating system can be applied to the substrate or previously applied coating layer according to any of a number of techniques well known in the art. These include, for example, spray coating, dip coating, roll coating, curtain coating, and the like. The electrodeposition coating is preferably applied by electrodeposition. For automotive applications, the disclosed film-forming coating composition and the topcoat layer or layers are preferably applied by spray coating, particularly electrostatic spray methods.

Coating layers of one mil or more are typically applied in two or more coats, separated by a time sufficient to allow some of the solvent or aqueous medium to evaporate, or "flash," from the applied layer. The flash may be at ambient or elevated temperatures, for example, the flash may use radiant heat.

In one embodiment, the layers described are cured with heat. Curing temperatures may be from 70 degree C. to 180 degree C., and particularly preferably from 170 degree F. to 200 degree F. (76 C to 93 C) for a composition including an unblocked acid catalyst, or from 240 degree F. to 325 degree F. (115 C to 163 C) for a composition including a blocked acid catalyst. Typical curing times at these temperatures range from 15 to 60 minutes, and preferably the temperature is chosen to allow a cure time of from 15 to 30 minutes. In a preferred embodiment, the coated substrate is an automotive body or part. The coats as applied can be from 0.5 mil up to 3 mils dry film build, and a sufficient number of coats are applied to yield the desired total film thickness of the multilayer coating system.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention is further described in the following examples. The examples are merely illustrative and do not in any way limit the scope of the invention as described and claimed.

EXAMPLES

Preparation of Polyester Binder used in the Examples

The polyester binder used to prepare the first coating compositions useful as primers is an aqueous polyester dispersion prepared from a combination of a series of monomers and a prepolymer.

The prepolymer is made by adding 307.8 parts by weight of neopentyl glycol to a 1000 ml reaction flask equipped with a stirrer and packed column for high temperature heating. Next, 72.4 parts of trimethylolpropane are added to the reaction flask. The mixture is stirred and heat is applied to the reaction flask via a heating mantle set for a target temperature of 100° C. (212° F.). Once a solution is obtained, 207.7 parts of adipic acid and 238.8 parts of isophthalic acid are added. The temperature of the mixture is then increased to 240° C. (464° F.) at a rate of 23.9° C. (75° F.) per hour. Once the targeted temperature is achieved, the reaction mixture is sampled every hour. The acid number of each hourly sample is determined. Samples are taken until the acid number is less than 7. Thereafter, the reaction mixture is cooled rapidly via a cooling bath of chilled water. Another sample is taken when the temperature of the reaction mixture has cooled to 150° C. (302° F.) to verify the final acid number. When the temperature reaches 120° C. (248 F), 247.0 parts of methyl isobutyl ketone is thoroughly mixed into the reaction mixture. Further addition of solvent can be made to achieve a targeted 80% solids.

For the second phase of the preparation of the polyester binder, the following reagents are added to a 1000 ml reaction flask: 56.34 parts by weight of fatty acid, 50.66 parts of 1,6-hexanediol, 58.98 parts of ethyl butyl propanediol, 57.21 parts isophthalic acid, 13.40 parts of trimethylolpropane and 7.08 parts of toluene. The reaction flask is next equipped with a packed column for high temperature heating. The reagents are mixed thoroughly and heat is applied over a period of 2 hours for a targeted temperature of about 230° C. (446° F.). The targeted temperature is maintained for one hour. Thereafter, samples are taken every 30 minutes for acid number determination. Once the acid number falls in the range of 9.5 to 10.5, heating is discontinued and the reaction mixture is cooled rapidly to 140° C. (284° F.). Next, 45.1 parts of trimellitic anhydride is added to the reaction mixture and heating is resumed for a targeted temperature of 170° C. (338° F.). After attaining 170° C., samples are taken every 30 minutes for acid number determination until the acid number value lies in the range of 52-55. The reaction mixture is then cooled to 120° C. (248° F.). Next, addition of 139.87 parts of the prepolymer prepared in the first phase is made to the reaction mixture along with 9.89 parts of methyl isobutyl ketone. The reaction mixture is stirred thoroughly for 30 minutes. The temperature of the mixture is then increased to 180° C. (356° F.). Removal of solvent is then initiated during this heating stage by vacuum. Samples are taken every 15 minutes until the acid number falls in the range to 29 to 31. Once the targeted acid number is attained, the mixture is cooled to 150° C. (302° F.). Addition of 31.67 parts of 3-methyl-3-methoxy-1-butanol is made to the mixture that is then stirred for another 30 minutes. The system is then cooled to 75° (167° F.) and the following are added: 10.66 parts of N,N-dimethylethanol amine, 93.4 parts methylated butylated melamine, 4.9 parts of polyether solution K2000, and 9.9 parts of 3-methyl-3-methoxy-1-butanol. Thorough mixing is conducted for a period of 30 minutes. Finally, 410.9 parts of deionized water are added to the batch and stirred thoroughly to achieve a homogeneous dispersion. The theoretical total non-volatiles are approximately 48 wt %.

Example 1

Primer with Titanium Dioxide Only

A primer composition was prepared by first mixing together 32.6 parts by weight of BAYHYDROL 140 AQ polyurethane dispersion (about 40% nonvolatile, 59% water, and 1% toluene, pH of about 6.0 to about 7.5, anionic DESMODUR W/1,6-hexamethylene diisocyanate/polyester polyol-based polyurethane, available from Bayer Corporation, Pittsburgh, Pa.), 122.3 parts by weight of an emulsion of an acrylic polymer (glass transition temperature of 20° C., nonvolatile content of about 41% in water, acid number of about 8 mg KOH/g nonvolatile, hydroxyl equivalent weight of 510, salted with 2-amino-2-methylpropanol to a pH of about 6 to 7), 26.9 parts deionized water, and 530.0 parts by weight of pigment paste (60% by weight nonvolatile in water, nonvolatiles are 21.7% by weight of BAYHYDROL 140 AQ polyurethane resin, 76.8% by weight of titanium dioxide, 1.5% carbon black, ground on a horizontal mill to a fineness of 6 microns). To this mixture were added 18.9 parts by weight of RESIMENE 747 (a melamine formaldehyde resin available from Solutia, St. Louis, Mo.) A total of 265 parts of a polyester resin (40% solids, Acid number 32). A total of 3.7 parts by weight of an additive package (flow additive and thickener) was then added. Finally, the pH of the primer composition was adjusted to about 8.0 with 2-amino-2-methylpropanol.

The primer composition had a nonvolatile content of 52% by weight. The volatile organic content of the primer composition was 85 grams/liter. The primer composition was adjusted before spray application with deionized water to a viscosity of 120 to 150 centipoise at 384 sec$^{-1}$.

Example 2

Primer with Titanium Dioxide and Barium Sulfate

A primer composition which included barium sulfate (BaSO$_4$) was prepared by first mixing together 30.2 parts by weight of BAYHYDROL 140 AQ polyurethane dispersion (about 40% nonvolatile, 59% water, and 1% toluene, pH of about 6.0 to about 7.5, anionic DESMODUR W/1,6-hexamethylene diisocyanate/polyester polyol-based polyurethane, available from Bayer Corporatio, Pittsburgh, Pa.), 113.1 parts by weight of an emulsion of an acrylic polymer (glass transition temperature of 20° C., nonvolatile content of about 41% in water, acid number of about 8 mg KOH/g nonvolatile, hydroxyl equivalent weight of 510, salted with 2-amino-2-methylpropanol to a pH of about 6 to 7), 24.9 parts deionized water, and 565.4 parts by weight of pigment paste (65.6% by weight nonvolatile in water, nonvolatiles are 17.2% by weight of BAYHYDROL 140 AQ polyurethane resin, 60.9% by weight of titanium dioxide, 1.2% carbon black and 20.7% barium sulfate, ground on a horizontal mill to a fineness of 6 microns). To this mixture were added 17.5 parts by weight of RESIMENE 747 (a melamine formaldehyde resin available from Solutia, St. Louis, Mo.) followed by addition of 245.0 parts of a polyester resin (40% solids, Acid number 32). Next, a total of 3.5 parts by weight of an additive package (flow additive and thickener) was added. Finally, the pH of the primer composition was adjusted to about 8.0 with 2-amino-2-methylpropanol. The primer composition had a nonvolatile content of 56% by weight. The volatile organic content of the primer composition was 85 grams/liter. The primer composition was adjusted before spray application with deionized water to a viscosity of 120 to 150 centipoise at 384 sec$^{-1}$.

Example 3

Primer with Titanium Dioxide and Talc

A primer composition which included talc (magnesium silicate) was prepared by first mixing together 31.3 parts by weight of BAYHYDROL 140 AQ polyurethane dispersion (about 40% nonvolatile, 59% water, and 1% toluene, pH of about 6.0 to about 7.5, anionic Desmodur W/1,6-hexamethylene diisocyanate/polyester polyol-based polyurethane, available from Bayer Corporatio, Pittsburgh, Pa.), 117.5 parts by weight of an emulsion of an acrylic polymer (glass transition temperature of 20° C., nonvolatile content of about 41% in water, acid number of about 8 mg KOH/g nonvolatile, hydroxyl equivalent weight of 510, salted with 2-amino-2-methylpropanol to a pH of about 6 to 7), 25.8 parts deionized water, and 548.4 parts by weight of pigment paste (65.4% by weight nonvolatile in water, nonvolatiles are 18.4% by weight of BAYHYDROL 140 AQ polyurethane resin, 65.5% by weight of titanium dioxide, 1.3% carbon black and 14.8% talc, ground on a horizontal mill to a fineness of 6 microns). To this mixture were added 18.2 parts by weight of RESIMENE 747 (a melamine formaldehyde resin available from Solutia, St. Louis, Mo.) followed by addition of 245.0 parts of a polyester resin (40% solids, acid number 32). Next, a total of 3.6 parts by weight of an additive package (flow additive and thickener) was added. Finally, the pH of the primer composition was adjusted to about 8.0 with 2-amino-2-methylpropanol. The primer composition had a nonvolatile content of 56% by weight. The volatile organic content of the primer composition is 85 grams/liter. The primer composition was adjusted before spray application with deionized water to a viscosity of 120 to 150 centipoise at 384 sec$^{-1}$.

Evaluation of the Disclosed Method

The primer compositions of Examples 1, 2 and 3 were applied to electrocoat primed 4" by 12" steel panels and cured for 25 minutes at 150° C. to form a primer layer of about 25 microns dry film thickness. The cured primer was then topcoated with commercial basecoat and clearcoat compositions. The panels were then subjected to gravelometer testing according to the test procedure of SAE J400. Briefly, in the SAE J400 procedure, the panels are cooled to −20° C. for 1 hour prior to the gravel test. The panel is positioned in a gravelometer machine in an upright position, 90° from path of gravel. One pint of gravel is blown onto the panel with an air pressure of 70 psi. The panel is then warmed to room temperature, tape pulled with 3M 898 strapping tape, and rated according to chip rating standards on a scale of 1 to 5, with 1 corresponding to a standard having more than 4% topcoat paint loss and 5 corresponding to a standard having less than 0.3% paint loss due to chipping. The gravelometer ratings for the panels obtained using the compositions of Examples 1, 2, and 3 are shown in the following table.

Evaluation of % Paint Loss per Gravelometer Testing

Each sample chip panel was first scanned using a Vieew digital image analyzer by Atlas Analytical Instruments. The digital image was evaluated using the Vieew software Aquinto a4i version 5.00 (level 593). The Particle Analysis procedure in the software was used to determine the actual percentage of paint loss by defining a color contrast to differentiate the failure mode at the substrate and at the primer. Each paint sample was analyzed in triplicates to obtain an average value of the % paint loss.

Fischer Microhardness

A Fischerscope® H100 C equipped with a pyramid shaped diamond indenter was used to measure the microhardness of the primer. The panel was placed on the stage of the instrument with the primer surface facing the indenter and secured with the instrument lever. The instrument was connected to a computer and was interactive via the WIN-HCU software so that measuring parameters could be defined. In the test setup procedure used, a maximum force of 25 mN was applied over a period of 20 seconds and held constant for a period of 5 seconds. The force was then unloaded from 25 mN over 20 seconds and maintained at minimum force for 5 second. A series of three readings was taken at 25 micron film build on the same sample panel at different spots, all in close proximity. The average of three sets of measurements was obtained and included HU, the universal hardness in N/mm$^2$; h max, the maximum indentation, in micrometers; Cr1, the Creep at maximum force in %; Cr2, the Creep at minimum force in %; Y, Young's Modulus in giga-Pascals and $W_e/W_{tot}$, the elastic deformation work of the total material deformation work in %.

TABLE 1

| Example | P/B Ratios TiO2/BaSO4/Talc | Chip Rating | % Paint Loss | Elastic Component % $W_e/W_{tot}$ |
|---|---|---|---|---|
| 1 | 0.9/0.0/0.0 | 4.0 | 0.40 | 27.4 |
| 2 | 0.9/0.3/0.0 | 2.5 | 0.91 | 22.7 |
| 3 | 0.9/0.0/0.2 | 3.0 | 0.80 | 24.9 |

It can be seen that the disclosed method can be used to predict the chip performance of a multilayer coating system as indicated below in Table 2. The % C.P. was calculated according to % C.P.=7.61636−0.225473 ($W_e/W_{tot}$). In all cases, the % C.P. correlates to a desirable % paint loss as evaluated per the above traditional gravelometer test.

TABLE 2

| | Example | | |
|---|---|---|---|
| | 1 | 2 | 3 |
| % $W_e/W_{tot}$ | 27.4 | 22.7 | 24.9 |
| % C.P. | 1.43 | 2.50 | 2.00 |
| % Paint Loss | 0.40 | 0.91 | 0.80 |

The disclosed method is advantageous because allows for the evaluation of the chip performance of a coated substrate without the costly and laborious test panel preparation associated with gravelometer testing practices. The disclosed method is also advantageous in that it provides a predication of the chip performance of a cured multilayer coating system comprising a cured film of a first coating system via the % C.P. of a cured film of the first coating system.

We claim:

1. A single measurement method of predicting chip performance of a cured coating system comprising a first coating composition, comprising providing a coated substrate comprising a substrate and a cured film of the first coating composition thereon, measuring elastic work energy ($W_e/W_{tot}$) of the cured film, and calculating a % C.P. of the coated substrate via the formula:

$$\% C.P. = 7.61636 - 0.225473(W_e/W_{tot})$$

wherein a 5 C.P. of no more than about 3.50% correlates to a total paint loss of no more than 5% of a coating system comprising the first coating composition.

2. The method of claim 1 wherein the method is nondestructive.

3. The method of claim 1 wherein the substrate comprises a steel substrate.

4. The method of claim 3 wherein the steel substrate has been electrocoated.

5. The method of claim 1 wherein the coated substrate consists of an electrocoated steel substrate and a cured film of the first coating composition thereon.

6. The method of claim 1 wherein the cured film of the first coating composition has a dry film build of from about 0.8 to 2.0 mil.

7. The method of claim 1 wherein the first coating composition is a primer.

8. The method of claim 1 wherein the first coating composition comprises
a film-forming binder, and
a pigment mixture, said pigment mixture present in a pigment to binder ratio of at least 0.8 and consisting of
(i) at least 80% of titanium dioxide by weight, based on the total weight of the pigment mixture, and
(ii) no more then 20% by weight of non-titanium dioxide pigments based on the total weight of the pigment mixture, said non-titanium dioxide pigments being selected from the group consisting of carbon black, talc, barium sulfate, magnesium silicate, and combinations comprising two or more of the foregoing.

9. The method of claim 8 wherein the first coating composition has adjusted VOC of no more then 100 g/L, is free of all pigments other then those in the pigment mixture, and has a viscosity of no more then 200 cps at 384 sec⁻.

10. The method of claim 1, wherein measuring elastic work energy $W_e/W_{tot}$ of the cured first coating comprises measuring microhardness.

11. The method of claim 10 wherein measuring microhardness of the cured first coating comprises measuring microhardness with an indentor or a nanoindentor.

12. The method of claim 10 wherein measuring microhardness further comprises measuring one more of the universal hardness, maximum indentation, Creep at maximum force, Creep at minimum force, Young's Modulus, or a combination of two or more of the foregoing, in addition to measuring elastic work energy ($W_e/W_{tot}$).

13. The method of claim 12 wherein measuring microhardness further comprises obtaining values for universal hardness, maximum indentation, Creep at maximum force, Creep at minimum force, and Young's Modulus, in addition to measuring elastic work energy ($W_e/W_{tot}$).

14. The method of claim 1 wherein the measured work energy ($W_e/W_{tot}$) is at least 20%.

15. The method of claim 1 wherein the measured work energy ($W_e/W_{tot}$) is from about 20% to about 35%.

16. The method of claim 1 wherein a % C.P. of equal to or less then about 3.1% correlates to a total paint loss of equal to or less then 2% of a multilayer coating system comprising a cured film of the first coating composition.

17. The method of claim 16 wherein the multilayer coating system further comprises a cured topcoat film.

18. The method of claim 17 wherein the cured topcoat film further comprises a cured clearcoat film and cured basecoat film.

19. A method predicting % gravelometer paint loss cured multilayer coating system comprising a first coating composition, consisting essentially of
providing a coated substrate consisting of an electrocoated substrate and a cured film of the first coating composition thereon,
measuring elastic work energy ($W_e/W_{tot}$) of the cured film, and
calculating a % C.P. of the cured film via the formula:

$$\% C.P. = 7.61636 - 0.225473(W_e/W_{tot})$$

wherein a % C.P. of equal to or less than about 3.5% correlates to a total paint loss of equal to or less then 5% of a multilayer coating system comprising a cured film of the first coating composition and a cured topcoat film.

* * * * *